United States Patent [19]
Corl et al.

[11] Patent Number: 6,025,670
[45] Date of Patent: *Feb. 15, 2000

[54] MINIATURE, HIGH EFFICIENCY DUAL FREQUENCY ULTRASONIC TRANSDUCER WITH SELECTABLE BEAMWIDTH

[75] Inventors: Paul D. Corl, Palo Alto; Michael C. Pao, San Jose; Vincent A. Barletta, Sunnyvale; Victor Chechelski, Mountain View, all of Calif.

[73] Assignee: Cardiometrics, Inc., Rancho Cordova, Calif.

[ * ] Notice: This patent is subject to a terminal disclaimer.

[21] Appl. No.: 09/025,540

[22] Filed: Feb. 18, 1998

Related U.S. Application Data

[62] Division of application No. 08/759,054, Dec. 2, 1996, Pat. No. 5,740,596, which is a continuation of application No. 08/447,993, May 23, 1995, Pat. No. 5,581,144, which is a continuation of application No. 08/178,081, Jan. 6, 1994, abandoned.

[51] Int. Cl.⁷ .................................................. H01L 41/08
[52] U.S. Cl. ............................................ 310/369; 310/334
[58] Field of Search ................................. 310/334–337, 310/369

[56] References Cited

U.S. PATENT DOCUMENTS

| | | | |
|---|---|---|---|
| 1,907,425 | 5/1933 | Marrison | 310/369 X |
| 3,136,381 | 6/1964 | Anderson | 310/369 X |
| 3,735,159 | 5/1973 | Murry | 310/334 |
| 4,123,681 | 10/1978 | Barlow | 310/369 X |
| 5,059,851 | 10/1991 | Corl et al. | 310/334 |
| 5,581,144 | 12/1996 | Corl et al. | 310/369 |
| 5,740,596 | 4/1998 | Corl et al. | 29/25.35 |

OTHER PUBLICATIONS

Kunkel, "Finite–Element Analysis of Vibrational Modes in Piezoelectric Ceramic Disks," IEEE, Transactions on Ultrasonics, Ferroelectrics and Frequency Control.

Brissaud, "Characterization of Piezoceramics," IEEE Transactions on Ultrasonics, Ferroelectrics and Frequency Control, vol. 38, No. 6, Nov. 1991.

*Primary Examiner*—Mark O. Budd
*Attorney, Agent, or Firm*—Flehr Hohbach Test Albritton & Herbert LLP

[57] ABSTRACT

Ultrasonic transducer with a selectable beamwidth comprising a body of piezoelectric material in the form of an annulus having an outer diameter D and a thickness T. The body has proximal and distal generally planar parallel surfaces and a centrally disposed hole extending therethrough. The body has a cylindrical wall with a width W extending from the hole to the outer diameter. The transducer is capable of operating at low and high resonance frequencies with the low frequency resonance being determined by the diameter D and an aspect ratio of D/T and the high frequency resonance being determined by the thickness T and an aspect ratio of W/T.

12 Claims, 1 Drawing Sheet

MINIATURE, HIGH EFFICIENCY DUAL FREQUENCY ULTRASONIC TRANSDUCER WITH SELECTABLE BEAMWIDTH

This is a division of Ser. No. 08/759,054, filed Dec. 2, 1996, now U.S. Pat. No. 5,740,596 which was a continuation of Ser. No. 08/447,993, filed May 23, 1995, U.S. Pat. No. 5,581,144, which was a continuation of Ser. No. 08/178,081, filed Jan. 6, 1994, abandoned.

This invention relates to a miniature, high efficiency dual frequency ultrasonic transducer with selectable beamwidth, an assembly thereof and method.

In U.S. Pat. No. 5,059,851, there is disclosed a miniature ultrasound transducer assembly which utilizes a transducer in the form of a disk without a hole. With such a disk, it is known that there are two strong resonances, one related to the lateral (diameter) resonance and one related to the thickness resonance. In such transducers, however, since the thickness is close to the diameter (typically, the diameter was approximately twice the thickness), there was a strong interaction between the diameter and thickness resonances. Attempts to optimize efficiency between the two resonances were found to be difficult to achieve because of the undesired coupling between the two resonance modes which caused inefficiencies. FIGS. 3 and 4 of U.S. Pat. No. 5,059,851 show a doughnut-shaped transducer. The specification suggests an appropriate aspect ratio of 0.5-to-1. The distance from the outer circumference to the outer margin of the hole would be approximately one-fourth to one-third of the width extending across the entire doughnut-shaped transducer. At the time of the disclosure in FIGS. 3 and 4, certain advantageous features of such a construction were not appreciated. There is therefore a need for a new and improved ultrasonic transducer, assembly thereof and method which takes full advantage of the characteristics of such a transducer.

In general, it is an object of the present invention to provide an ultrasonic transducer, assembly thereof and method which is capable of dual frequency operation providing selectable beamwidth.

Another object of the invention is to provide a transducer of the above character which although of miniature size is of high efficiency.

Another object of the invention is to provide a transducer and method of the above character in which efficient broadband operation can be achieved.

Another object of the invention is to provide a transducer assembly and method of the above character which is particularly applicable to intravascular Doppler transducers for coronary or cerebral applications.

Another object of the invention is to provide a transducer assembly and method of the above character which is capable of operating in the 5–20 MHz range.

Additional objects and features of the invention will appear from the following description in which the preferred embodiment is set forth in detail in conjunction with the accompanying drawings.

Figure 1:
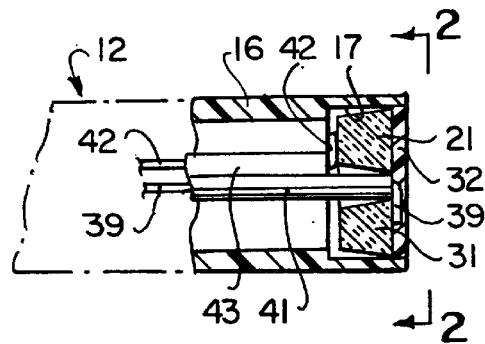
FIG. 1 is an enlarged cross-sectional view of a transducer and an assembly thereof incorporating the present invention.
Figure 2:
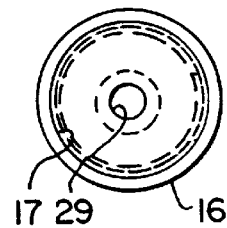
FIG. 2 is an end elevational view looking along the line 2—2 of FIG. 1.

The ultrasonic transducer of the present invention is comprised of a body of piezoelectric material in the form of an annulus having a centrally disposed hole extending therethrough. It has an outer diameter D and proximal and distal generally planar surfaces. An electrode covers each of the proximal and distal planar surfaces. The piezoelectric material also has a thickness T extending from the proximal to the distal surfaces and a wall width W extending from the outer margin of the hole to the outer diameter. The body is capable of operating at a low resonance frequency and a high resonance frequency. The low frequency resonance is principally determined by the diameter D and the aspect ratio of D/T. The high frequency resonance is principally determined by the thickness T and the aspect ratio of W/T.

More in particular, the transducer assembly 11 incorporating the present invention forms a part of a guide wire 12 which is of the type described in U.S. Pat. No. 5,059,851. This guide wire 12 as described therein is typically comprised of a flexible elongate member in the form of a stainless steel tube having a suitable length as for example 150 cm. This flexible elongate member can have a suitable diameter ranging from 0.018" to 0.010". The flexible elongate member is provided with a passageway extending the length thereof. The distal extremity of the flexible elongate member may typically be secured to a coil spring and the coil spring is secured to a cylindrical tip 16 which as described therein may be secured to the distal extremity of the spring by having the coil spring threaded onto the tip 16. The tip 16 is provided with a cup-shaped cylindrical recess 17 which receives the transducer 21 of the present invention.

The transducer 21 is formed of a body 22 of a material of the type described in U.S. Pat. No. 5,059,851 as for example a piezoelectric material suitable for use as an ultrasonic as for example a piezoelectric ceramic. One piezoelectric ceramic found to be particularly satisfactory is EC-98 lead magnesium niobate available from EDO Corporation, Wester Division, Ceramics Division, 2645 South 300 West, Salt Lake City, Utah 84115. The EC-98 composition was selected because it provides a higher dielectric constant, low aging characteristics, excellent coupling characteristics and a high strain constant which makes it particularly suitable for miniature transducers of the present invention.

The body 24 which has been formed as hereinafter described has the form of an annulus or ring and can be characterized as being doughnut shaped. The body 24 has substantially planar proximal and distal parallel surfaces 26 and 27 with the distal surface 27 facing distally or outwardly from the distal extremity of the guide wire 12 as shown in FIG. 1. The body 24 is provided with an outer cylindrical surface 28 which extends in a direction generally perpendicular to the planar surfaces 26 and 27. The body 24 is also provided with a centrally disposed hole 29 which extends through the surfaces 26 and 27 at substantially right angles thereto.

The transducer assembly 11 is particularly constructed to be used in small-diameter guide wires as for example those ranging below 0.018" and below. The transducer 21 therefore must have correspondingly small dimensions so they can be utilized in the distal extremities of such guide wires.

In order to achieve reliable manufacture of such transducers, it has been found desirable to utilize laser machining. Such laser machining forms cuts and holes with slight tapers, as for example 5° or less which are shown in exaggerated form in FIG. 3. In connection with the present invention to provide such transducers 21, a sheet (not shown) of the piezoelectric material having the desired thickness as for example 3.8 mils is used. The transducers 21 are formed by a step-and-repeat process from the sheet of material. The amount of taper is determined by the type of laser being utilized and the focal length of the objective lens for the laser beam. By providing a lens having an increased focal length it is possible to reduce the taper. By utilizing an X-Y motion table in conjunction with a YAG laser, it has been found that it is possible to provide a laser having a spot size ranging from 0.8 to 1.0 mil and having a pulse repetition rate ranging from 50 to 150 Hz to cut both the outside diameter and the inside diameter for the transducer to provide the cylindrical body 22 with the hole 29 extending centrally therethrough. Good results were achieved utilizing a YAG laser having an operating frequency of 1064 nanometers.

It should be appreciated that other types of lasers can be used. For example, an excimer laser can be utilized and may be desirable because it has a low thermal distortion but the cut rates are less than that which can be accomplished with a YAG laser. The excimer laser typically operates at 308 nm.

With the use of the YAG laser, it is possible to produce the transducers 21 at a relatively rapid production rate with minimal damage to the crystalline structure. It has been found that any material evaporated onto the surfaces 26 and 27 of the body 22 during the laser machining operation can be readily removed with a suitable solvent such as acetone or alcohol utilizing a Q-tip. Thus there remains a very small heat affected zone near the outer perimeter of the hole 29 adjacent the cylindrical surface 28 and the inner perimeter adjacent the hole 29.

In order for the transducer 21 to fit within the cylindrical recess 17 of the tip 16, the transducer 21 should have an appropriate diameter. Thus, by way of example, for a guide wire having an outside diameter of 0.014", the transducer 21 should have an outside diameter of approximately 0.010". Using laser machining for such a size transducer it has been possible to achieve the cylindrical surfaces 28 and the hole 29 in the surfaces 26 and 27 with a taper of approximately 5°. This taper can be improved to approximately 2–3° with an objective lens having a longer focal length.

In connection with the present invention of a guide wire 12 of the type shown in FIG. 1, it is desirable that the transducer 21 produce a broad beam to make it possible to cover as wide a cross-section as possible of the vessel in which it is disposed, and preferably to extend to the side walls of the vessel so that it is ensured that the velocity of the liquid, as for example blood, flowing through center of the lumen is accurately measured by ensuring that the beam covers at least the center of the vessel lumen.

As mentioned previously, the preferred sizes for intravascular guidewires are in the range of 0.010" to 0.018" diameter, with some as large as 0.030" or greater. The optimum Doppler frequencies for intravascular operations (considering attenuation, backscatter efficiency, scanning distance, etc.) are typically in the range of 5–20 MHz (corresponding to acoustic wavelengths in blood of 0.003 inch to 0.012 inch). These ranges for transducer size and ultrasound wavelength correspond to acoustic transducers having diameters ranging from approximately 1 to 10 wavelengths, with the most desirable combinations being transducers having diameters in the range of 1 to 5 wavelengths.

In connection with the present invention, it has been found to be desirable to utilize the doughnut-shaped or ring-type transducer 21 which has the capability of providing two strong resonant frequencies, one of which can be characterized as high-resonant frequency and the other of which can be characterized as a low-resonant frequency.

The low resonant frequency is strongly related to the largest dimension of the transducer 21 which is the outside diameter D. The resonance can be characterized by its frequency and efficiency. These parameters can be predicted using a standard model for disk-shaped transducers. For example, Kunkel et al. in *Finite-Element Analysis of Vibrational Modes in Piezoelectric Ceramic Disks*, IEEE, Vol. 37, No. 4, July 1990 use finite element analysis to calculate the normalized resonance frequency and the electromechanical coupling coefficient (which is an important element of transducer efficiency) as a function of the diameter to thickness aspect ratio D/T of a ceramic disk transducer. The diameter D can then be used to transform the normalized resonance frequency to an actual resonance frequency. The centrally disposed hole 29 has only a small effect on the frequency and electromechanical coupling coefficient of the fundamental low frequency mode, but it does act to suppress many of the undesirable disk modes which would otherwise waste energy and thereby reduce the efficiency of the transducer. Thus the ring-type transducer offers the possibility of an efficient low frequency transducer, with a very pure resonant mode and weak harmonics.

The second or higher frequency resonant mode is strongly related to the cross section of the doughnut-shaped or ring-type transducer. The resonance can be characterized by its frequency and efficiency. These parameters can be predicted using a standard model for linear transducers of rectangular cross section, since the ring-type transducer can be envisioned as a linear element bent into a ring shape. Mason in *Physical Acoustics Principles and Methods*, Academic Press, Vol. I, Part A, 1964 used analytical techniques to calculate the normalized resonance frequency and electromechanical coupling coefficient (which is an important element of transducer efficiency), as a function of the width to thickness aspect ratio W/T of the ring cross section. The thickness T can then be used to transform the normalized resonance frequency into an actual resonance frequency. For width to thickness aspect ratios less than 1, the fundamental resonance mode for a rectangular cross section is often referred to as the length extensional mode. Theory predicts, and experiments confirm that the electromechanical coupling coefficient is maximized for a width to thickness aspect ratio of approximately 0.6, and this coupling coefficient is significantly higher than that found in a conventional thickness mode resonance transducer.

Proper choice of the three key transducer dimensions, diameter D, thickness T, and annular width W permits the efficient operation of a miniature transducer at two distinct frequencies. The centrally disposed hole suppresses the unwanted disk resonance modes, and permits efficient operation using a low frequency lateral resonant mode. At the same time the centrally disposed hole permits the transducer to take advantage of the efficient length expander mode of vibration in the thickness resonant mode, with the aspect ratio W/T close to the theoretical optimum of approximately 0.6.

In the past in connection with transducers it was typically desired to provide a transducer which has a single mode of operation with the other frequency modes being unwanted. In the present application, the present transducer takes advantage of an unwanted mode by creating a low-frequency lateral mode to provide a transducer which has two strong modes and wherein other spurious modes have been limited to provide a dual-frequency transducer to optimize the operation of the guide wire 12 as hereinafter described. It should be appreciated that either one of the two resonant frequencies may be chosen to be optimized to provide the best performance for a specific application at the expense of foregoing the flexibility of dual frequency operation. It can be further appreciated that if the high and low resonant frequencies are designed to be close to one another, the two resonances will blend together to provide a single broad resonance, thereby providing an efficient broadband transducer design.

By way of example, a transducer 21 incorporating the present invention had a diameter D extending across the distal surface 27 of 10.2 mils and a diameter D extending along the proximal surface 26 of 9.4 mils. It had a thickness T of 3.8 mils. The hole 29 had a diameter at the proximal surface 26 of 3.3 mils and a diameter at the distal surface 27 of 2.5 mils. With such dimensions, the distance W from the outer margin of the hole 29 to the outer surface 28 was 3.85 mils at the distal surface 27 and 3.0 mils at the proximal surface 26. The transducer 21 was mounted in the cup-shaped cylindrical recess 17 by suitable means such as a medical-grade adhesive of the type disclosed in U.S. Pat. No. 5,059,851. Also a matching layer 32 was provided at the distal surface 27 of a suitable material such as described in U.S. Pat. No. 5,059,851 to provide a flush surface and to fill the recess 17 as shown particularly in FIG. 1. Such a transducer 21 was found to have a low-frequency mode of operation of approximately 6.5 MHz and a high-frequency resonance of 15.0 MHz. For other dual frequencies of 6.0 MHz and 10.0 MHz the transducer 21 would have a diameter D extending across the distal surface, would be approximately 10.8 mils and the thickness T would be approximately 6.7 mils. For dual frequencies of 6.0 MHz and 12.0 MHz, the transducer 21 would have a diameter D extending across the distal surface, would be approximately 10.5 mils and the thickness T would be approximately 5.2 mils.

Figure 3:
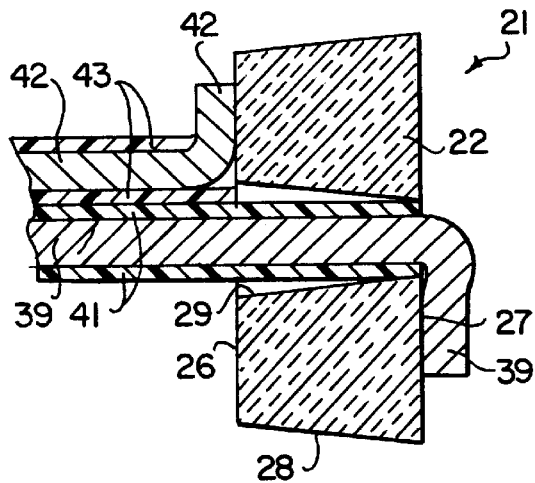
FIG. 3 is an enlarged cross-sectional view of the transducer shown in FIG. 1.
Figure 4:
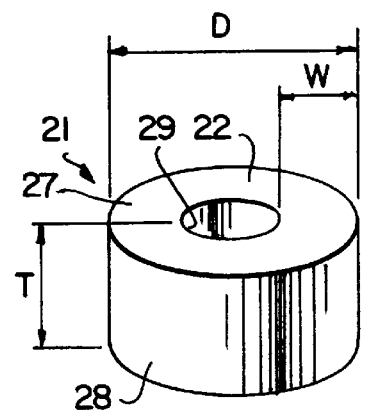
FIG. 4 is an enlarged isometric view of the transducer shown in FIG. 3.
Figure 5:
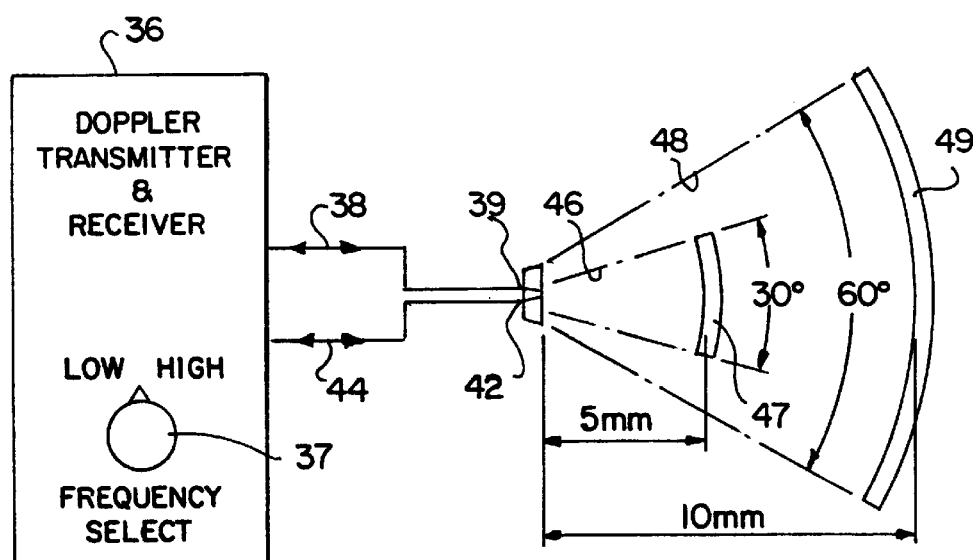
FIG. 5 is a block diagram and a schematic illustration showing the manner in which selectable beam width can be achieved utilizing the transducer shown in FIGS. 1 through 4.

The transducer 21 was activated at these frequencies by a conventional power supply, transmitter and receiver represented by the block 36 in FIG. 5. The block 36 was provided with a frequency select switch 37 which has the capability of selecting various frequencies as for example a specific low frequency or a specific high frequency from a range of frequencies as for example 5 Mhz, 6 MHz, 7.5 MHz, 10 MHz, 12 MHz, 15 MHz and 20 MHz. These selected frequencies were applied to a pair of lines 38 and 44 connected to a pair of insulated conductors 39 and 42. The conductor 39 extends through the hole 29 and was bent over and soldered to the distal surface 27 of the transducer 21 as shown in FIG. 3. The conductor 39 was provided with an insulating covering 41. The conductor 42 was provided and had its distal extremity bent and soldered to the proximal surface 26 of the transducer 21. It was also provided with an insulating covering 43. The Doppler transmitter from the block 36 supplied pulses of electrical energy to the ultrasonic transducer 21 which produced ultrasonic pulses that were propagated outwardly from the distal surface 27 in a forwardly extending conically-shaped beam 46 in which the conical beam subtended an angle or had a beam width of approximately 30° to analyze a sample volume 47 at a suitable distance as for example approximately 5 mm from the distal surface 27. When the transducer 21 was excited at the low frequency, a conical-shaped beam 48 was propagated forwardly and subtended an angle or had a beam width of approximately 60° to analyze a sample volume 49 as shown in FIG. 5 at a distance of approximately 10 mm from the distal surface 27. In general, the width of the beam from a small ultrasonic transducer (expressed in radians is $\lambda/D$, where $\lambda$ is the wavelength of the ultrasound and D is the transducer diameter, a lower frequency (with its corresponding longer wavelength) will provide a proportionally broader beam compared to higher frequency operation.

In making Doppler blood flow measurements with the guide wire 12 having a transducer assembly 11 of the present invention mounted thereon, it is important that the beam propagated by the transducer covers at least the central region of the vessel to properly ascertain spatial peak blood flow, because it is in this region that the blood is flowing at the fastest rate. Thus in order to be sure that the proper blood flow is being measured, it may be desirable to utilize the lower operating frequency with its corresponding wider beam to ensure that substantially all of the cross-sectional area of a measurement location of a vessel, or at least a substantial portion of the same which includes the central region of the vessel is covered by the ultrasound beam. However, if the ultrasound beam is much larger than the vessel, a great deal of acoustic energy will be lost as the beam spreads beyond the vessel walls. Thus in order to ensure that the Doppler signal is as strong as possible, it may be desirable to utilize the higher operating frequency with its corresponding narrower beam as long as the beam is large enough to cover a substantial portion of the vessel. For example, with a large vessel as for example a femoral artery having a 10 mm diameter, there is an excellent opportunity to pick up the central flow in the artery with the wider beam 48, whereas this might be difficult to do with the smaller beam 46. Conversely, in the case of a small vessel as for example a coronary artery having a diameter of 3 mm, the narrower beam 46 will be adequate to cover a substantial portion of the vessel, whereas the wider beam 48 might provide a weak Doppler signal. Thus, with the present invention, it is possible to make accurate measurements in a wide range of vessel sizes even though the distal extremity of the guide wire may be bent to accommodate passing into side branches and tortuous vessels and thus may not be centered in the vessel.

From the foregoing it can be seen that there has been provided a transducer assembly for use on a guide wire which is particularly adapted to making flow measurements in a vessel in a body as for example the human body. The transducer is one which has dual-frequency operation with high and low resonance frequencies which are substantially equally efficient. By utilizing such a transducer, a method can be utilized to provide narrow and wide beams to ensure that at least the center of the vessel where maximum flow occurs will be in the sample volume being measured.

What is claimed is:

1. An ultrasonic transducer capable of operation at a low frequency resonance and at a high frequency resonance, comprising an annular body of piezoelectric material with an axially extending hole, an outer diameter D, a thickness T, and a width W extending from the hole to the outer diameter, the low frequency resonance being determined by the diameter D and an aspect ratio D/T, and the high frequency resonance being determined by the thickness T and an aspect ratio W/T.

2. The transducer of claim 1 wherein the body has a generally cylindrical outer surface and generally planar proximal and distal end surfaces the hole extends in a direction perpendicular to the proximal and distal generally planar surfaces.

3. The transducer of claim 2 wherein the generally cylindrical outer surface and the hole are tapered.

4. The transducer of claim 3 wherein the distal surface has a diameter of approximately 10.2 mils, the proximal surface has a diameter of approximately 9.4 mils, and the thickness of the body is approximately 3.8 mils.

5. The transducer of claim 4 wherein the hole has a diameter of approximately 2.5 mils at the distal end surface and a diameter of approximately 3.3 mils at the proximal end surface.

6. The transducer of claim 1 wherein the low resonance frequency is approximately one-half of the high resonance frequency.

7. The transducer as in claim 6 wherein said low frequency resonance is at 6.5 MHz and the high frequency resonance is at 15.0 MHz.

8. The transducer of claim 7 wherein the transducer produces a beam having a width of approximately 60° at the low frequency resonance and a width of approximately 30° at the high frequency resonance.

9. The transducer of claim 1 wherein piezoelectric material has a high dielectric content, low aging characteristics, excellent coupling characteristics and a high strain constant.

10. The transducer of claim 9 wherein the piezoelectric material is EC-98.

11. A transducer assembly comprising a cylindrical tip of 0.018" or less in diameter and having an outwardly facing cup-shaped recess provided therein, an ultrasonic transducer formed of a piezoelectric material disposed in the recess, said body being in the form of an annulus having a centrally disposed hole extending therethrough and an outer diameter and proximal and distal parallel, generally planar surfaces and having a thickness of T extending from the proximal to the distal surfaces and a wall width of W extending from the outer margin of the hole to the outer diameter, adhesive means securing said body in said recess, a first conductor extending through the hole and being bonded to the distal surface, and a second conductor bonded to the proximal surface, the transducer being capable of operating at a low resonance frequency determined by the diameter D and an aspect ratio D/T and at a high resonance frequency determined by the thickness T and an aspect ratio W/T.

12. The assembly of claim 11 wherein the aspect ratio W/T is equal to approximately 0.6.

* * * * *